(12) United States Patent
Ozawa et al.

(10) Patent No.: US 9,861,825 B2
(45) Date of Patent: Jan. 9, 2018

(54) ORIENTATION AND PLACEMENT OF INDUCTIVE COMPONENTS TO MINIMIZE NOISE COUPLING TO A COMMUNICATION COIL IN AN IMPLANTABLE MEDICAL DEVICE

(71) Applicant: Boston Scientific Neuromodulation Corporation, Valencia, CA (US)

(72) Inventors: Robert D. Ozawa, Woodland Hills, CA (US); Damon Moazen, Northridge, CA (US); Robert G. Lamont, Van Nuys, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 56 days.

(21) Appl. No.: 14/525,925

(22) Filed: Oct. 28, 2014

(65) Prior Publication Data

US 2015/0134029 A1    May 14, 2015

Related U.S. Application Data

(60) Provisional application No. 61/902,089, filed on Nov. 8, 2013.

(51) Int. Cl.
*A61N 1/372* (2006.01)
*A61N 1/36* (2006.01)
(Continued)

(52) U.S. Cl.
CPC ..... *A61N 1/37229* (2013.01); *A61N 1/36125* (2013.01); *A61N 1/3782* (2013.01);
(Continued)

(58) Field of Classification Search
CPC ............ A61N 1/36125; A61N 1/37229; A61N 1/37211; A61N 1/3782; A61N 1/3787
See application file for complete search history.

(56) References Cited

U.S. PATENT DOCUMENTS 6,298,271 B1    10/2001    Weijand
6,516,227 B1    2/2003    Meadows et al.
(Continued)

FOREIGN PATENT DOCUMENTS

JP      10-314138 A     12/1998

OTHER PUBLICATIONS

International Search Report and Written Opinion regarding corresponding PCT Application No. PCT/US2014/062920, dated Jan. 23, 2015.

(Continued)

*Primary Examiner* — Joseph Dietrich
(74) *Attorney, Agent, or Firm* — Lewis, Reese & Nesmith, PLLC (57) ABSTRACT

Preferred orientations and placements of an inductor relative to a communication coil in an Implantable Medical Device (IMD) are disclosed. The inductor can comprise part of a boost converter used to generate a power supply voltage in the IMD, which inductor may interfere with the coil. The inductor may have a length defined by its windings around an axis, which axis may be in a plane of the coil or in a plane parallel to the coil. The inductor can be included within the area extent of the coil, and is preferably oriented such that its axis is parallel to a maximum dimension of the coil. Ends of the inductor are further preferably equidistant from the coil. So oriented and placed, the inductor is less prone to interfering with the coil, thus improving communications with the IMD.

24 Claims, 10 Drawing Sheets

(51) Int. Cl.
  *A61N 1/378*  (2006.01)
  *H04B 5/00*  (2006.01)
(52) U.S. Cl.
  CPC ........ *A61N 1/3787* (2013.01); *A61N 1/37211* (2013.01); *H04B 5/0075* (2013.01)

(56) References Cited

U.S. PATENT DOCUMENTS

| | | |
|---|---|---|
| 6,567,703 B1 | 5/2003 | Thompson et al. |
| 8,538,545 B2 | 9/2013 | Meskens |
| 2005/0017054 A1 | 1/2005 | Iverson et al. |
| 2008/0172109 A1 | 7/2008 | Rahman et al. |
| 2010/0211132 A1 | 8/2010 | Nimmagadda et al. |
| 2011/0112610 A1 | 5/2011 | Rahman et al. |
| 2011/0112612 A1 | 5/2011 | Rahman |
| 2012/0119698 A1 | 5/2012 | Karalis et al. |
| 2013/0331910 A1 | 12/2013 | Lamont et al. |
| 2014/0055088 A1* | 2/2014 | Joshi ................. H02J 7/025 320/108 |

OTHER PUBLICATIONS

U.S. Appl. No. 61/874,194, Bunyan et al., filed Sep. 5, 2013.
U.S. Appl. No. 61/874,863, Kothandaraman, filed Sep. 6, 2013.
U.S. Appl. No. 61/887,237, Feldman et al., filed Oct. 4, 2013.
Communication Pursuant to Article 94(3) EPC regarding corresponding EP Application No. 14796976.0, dated Sep. 22 2017.

* cited by examiner

ORIENTATION AND PLACEMENT OF INDUCTIVE COMPONENTS TO MINIMIZE NOISE COUPLING TO A COMMUNICATION COIL IN AN IMPLANTABLE MEDICAL DEVICE

CROSS REFERENCE TO RELATED APPLICATIONS

This is a non-provisional of U.S. Provisional Patent Application Ser. No. 61/902,089, filed Nov. 8, 2013, to which priority is claimed, and which is incorporated herein by reference in its entirety.

FIELD OF THE INVENTION

The present invention relates to improving wireless communications in an implantable medical device such as an implantable pulse generator.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical device or in any implantable medical device system.

Figure 1:
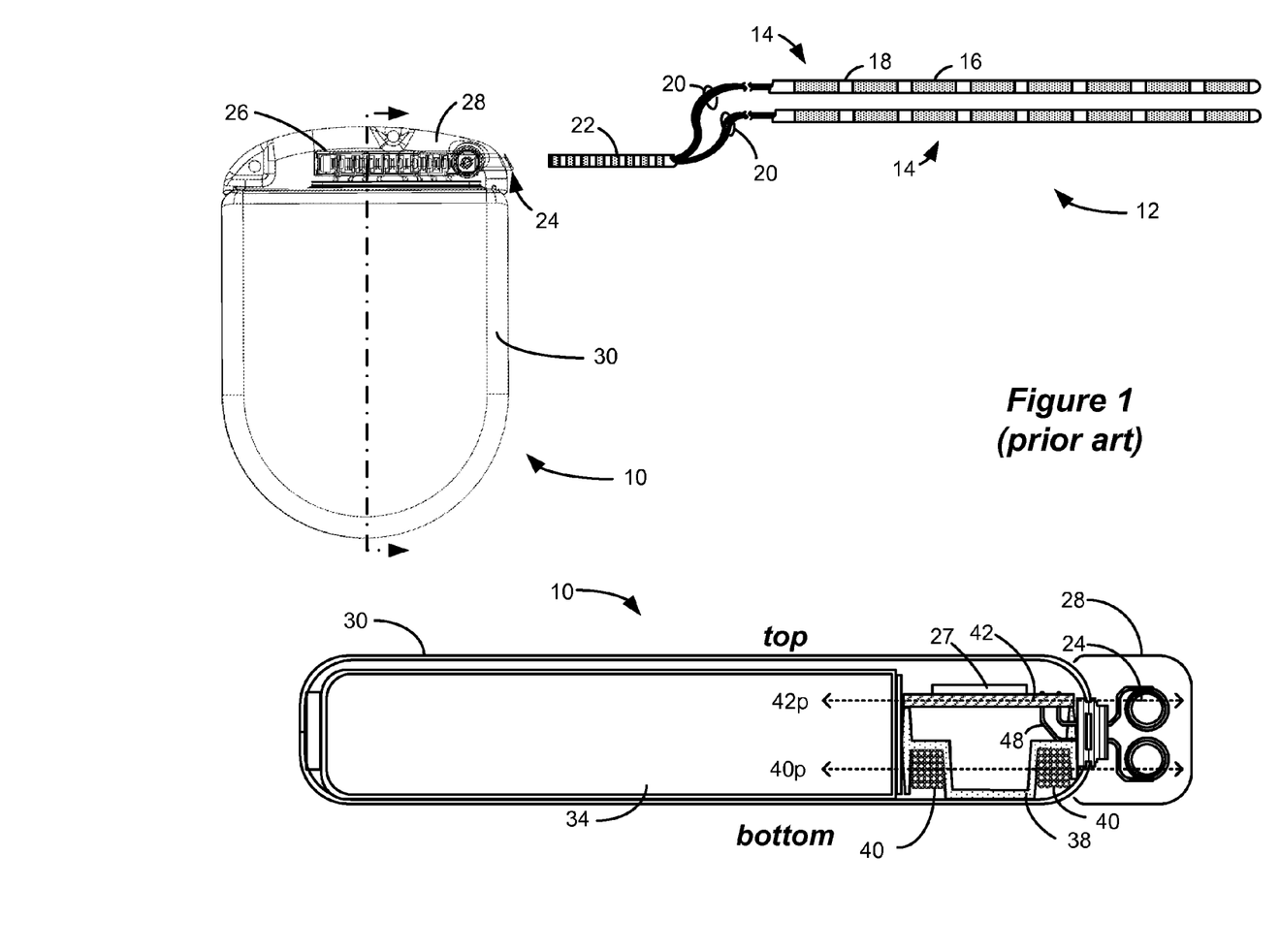
FIG. 1 shows an Implantable Pulse Generator (IPG) in accordance with the prior art.

An SCS system typically includes an Implantable Pulse Generator (IPG), such as that described in U.S. Provisional Patent Application Ser. No. 61/874,194, entitled "Construction for an Implantable Medical Device Employing an Internal Support Structure," filed Sep. 5, 2013, which is incorporated herein by reference. The IPG 10 of the '194 Application is shown in FIG. 1 in plan and cross sectional views, and includes a biocompatible device case 30 that holds the circuitry 27 and battery 34 necessary for the IPG to function. The IPG 10 is coupled to electrodes 16 via one or more electrode leads 14 that form an electrode array 12. The electrodes 16 are carried on a flexible body 18, which also houses the individual signal wires 20 coupled to each electrode 16. The signal wires 20 are also coupled to proximal contacts 22, which are insertable into lead connectors 24 fixed in a header 28 on the IPG 10, which the header can comprise an epoxy for example. Once inserted, the proximal contacts 22 connect to header contacts 26 in the lead connectors 24, which header contacts 26 are in turn coupled by feedthrough pins 48 (FIG. 2) to circuitry within the case 30. In the illustrated embodiment, there are sixteen electrodes 16 split between two leads 14, although the number of leads and electrodes is application specific and can vary. In an SCS application, electrode leads 14 are typically implanted on the right and left side of the dura within a patient's spinal cord. The proximal contacts 22 are then tunneled through the patient's tissue to a distant location where the IPG case 30 is implanted, at which point they are coupled to the lead connectors 24.

Figure 2:
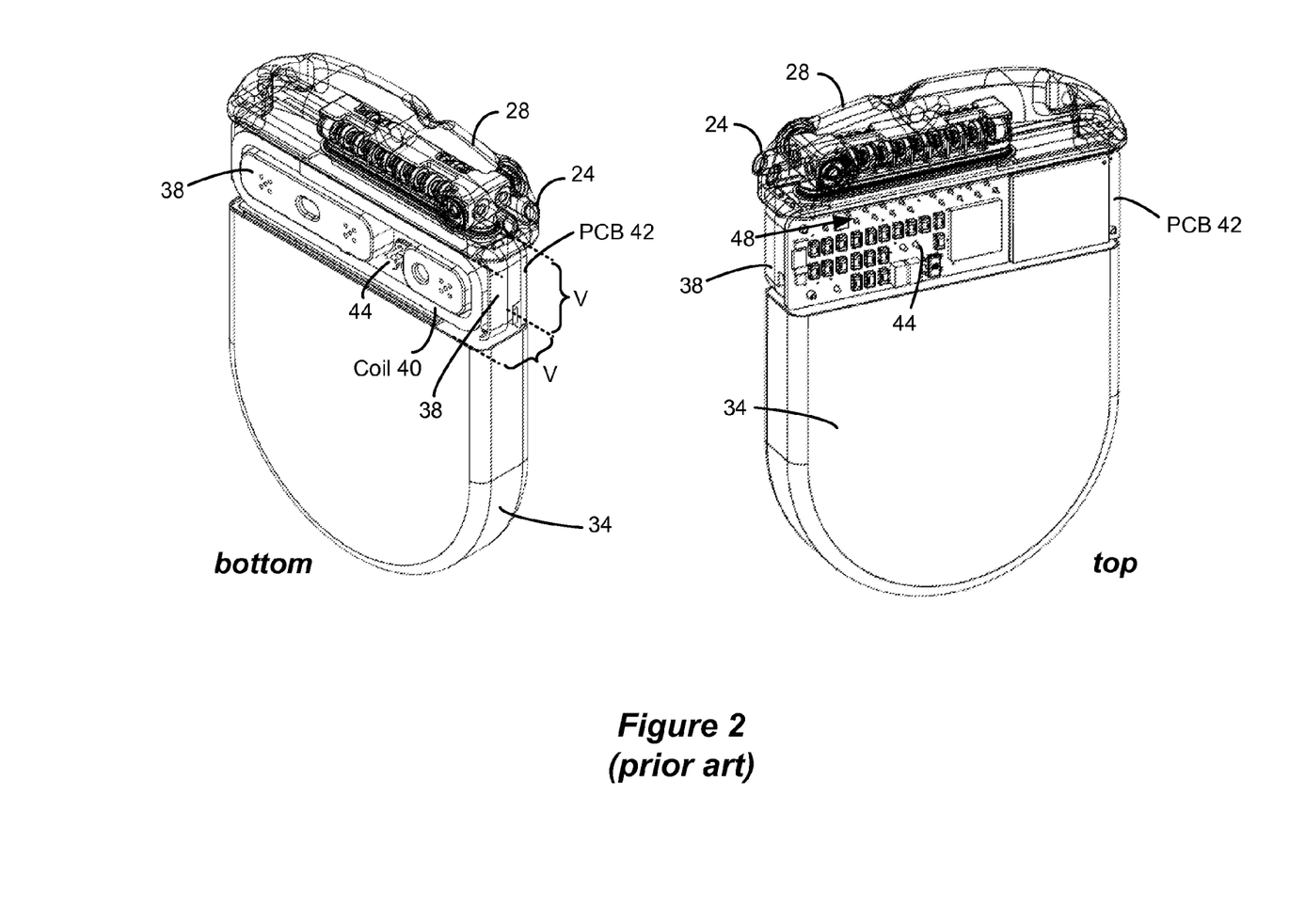
FIG. 2 shows the IPG with its case removed in accordance with the prior art.

FIG. 2 shows perspective views of the bottom and top sides of the IPG 10 with the case 30 removed so that internal components can be seen, including the battery 34, a communication coil (antenna) 40, and a printed circuit board (PCB) 42. As explained in the '194 Application, these components are affixed to and integrated using a rigid (e.g., plastic) support structure 38. Battery 34 in this example is a permanent, non-wirelessly-rechargeable battery. (Battery 34 could also be rechargeable, in which case either communication coil 40 or another recharging coil would be used to wirelessly receive a charging field that is rectified to charge the battery 34). The communication coil 40 enables bi-directional communication between the IPG 10 and a device external to the patient (FIG. 3) via magnetic induction. The ends of communication coil 40 are soldered to coil pins 44 molded into the support structure 38 to facilitate the communication coil 40's eventual connection to the PCB 42. PCB 42 integrates the various circuitry 27 needed for operation of the IPG 10. Communication coil 40 is proximate to the bottom side of the IPG 10 in plane 40$p$, while the PCB 42 is proximate to the top side in plane 42$p$, as shown in the cross section of FIG. 1.

Figure 3:
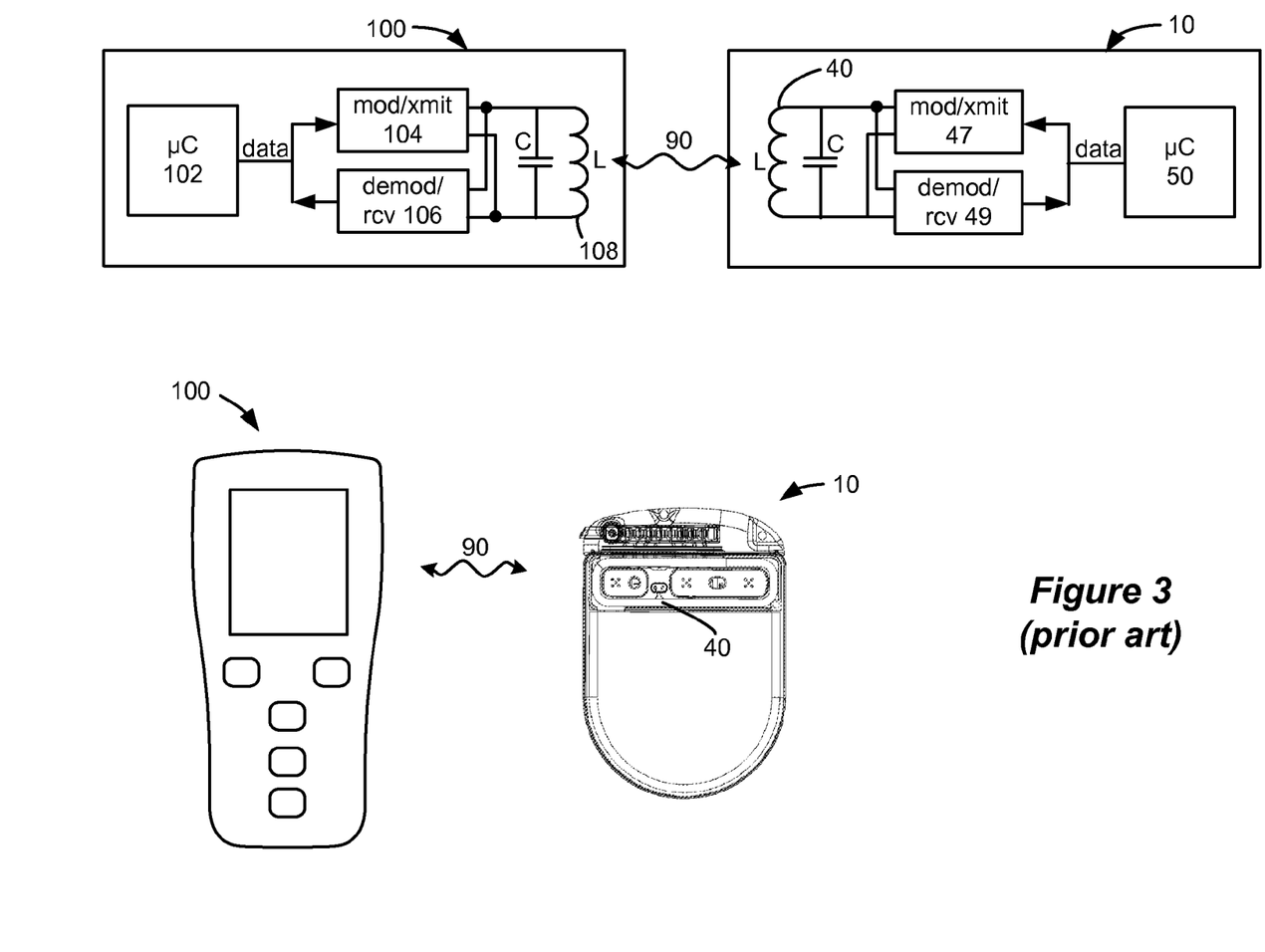
FIG. 3 shows the IPG in communication with an external controller, and the circuitry involved in each, in accordance with the prior art.

FIG. 3 shows an external controller 100 with a coil 108 for communicating with the IPG 10's communication coil 40 via a magnetic induction link 90. External controller 100 is preferably hand-holdable and portable, and includes a user interface (a display, buttons, etc.) to allow a user to adjust the therapeutic current that the IPG 10 is providing (e.g., to increase or decrease the stimulation being provided, to change which electrodes are providing the stimulation, etc.), and to review status information reported by the IPG 10.

In traditional SCS systems, data is bi-directionally transmitted along link 90 using a Frequency Shift Keying (FSK) protocol, in which a serial string of bits is wirelessly transmitted at different frequencies around a center frequency (e.g., fc=125 kHz). For example, if a '0' bit is to be transmitted to the IPG 10, control circuitry 102 in the external controller 100 (e.g., a microcontroller) provides that bit digitally to modulator/transmitter circuitry 104 in the external controller 100. The modulator/transmitter 104 tunes coil 108 to resonate at 121 kHz for example for a bit duration (e.g., 250 microseconds). This frequency is transmitted via link 90 to the communication coil 40 in the IPG 10, whose demodulator/receiver circuitry 49 decodes it per its frequency as a digital '0', and reports it to the IPG's control circuitry 50 (e.g., a microcontroller) for interpretation. A '1' bit would be transmitted similarly, but at a different frequency, for example 129 kHz. Transmission of data from the IPG 10 to the external controller 100 occurs similarly via modulator/transmitter circuitry 47 in the IPG 10 and demodulator/receiver circuitry 106 in the external controller 100.

Wireless communications between the external controller 100 and IPG 10 can occur in different manners, and external controller can be differently configured, as explained in U.S. Patent Application Ser. No. 61/874,863, filed Sep. 6, 2013.

Figure 4A:
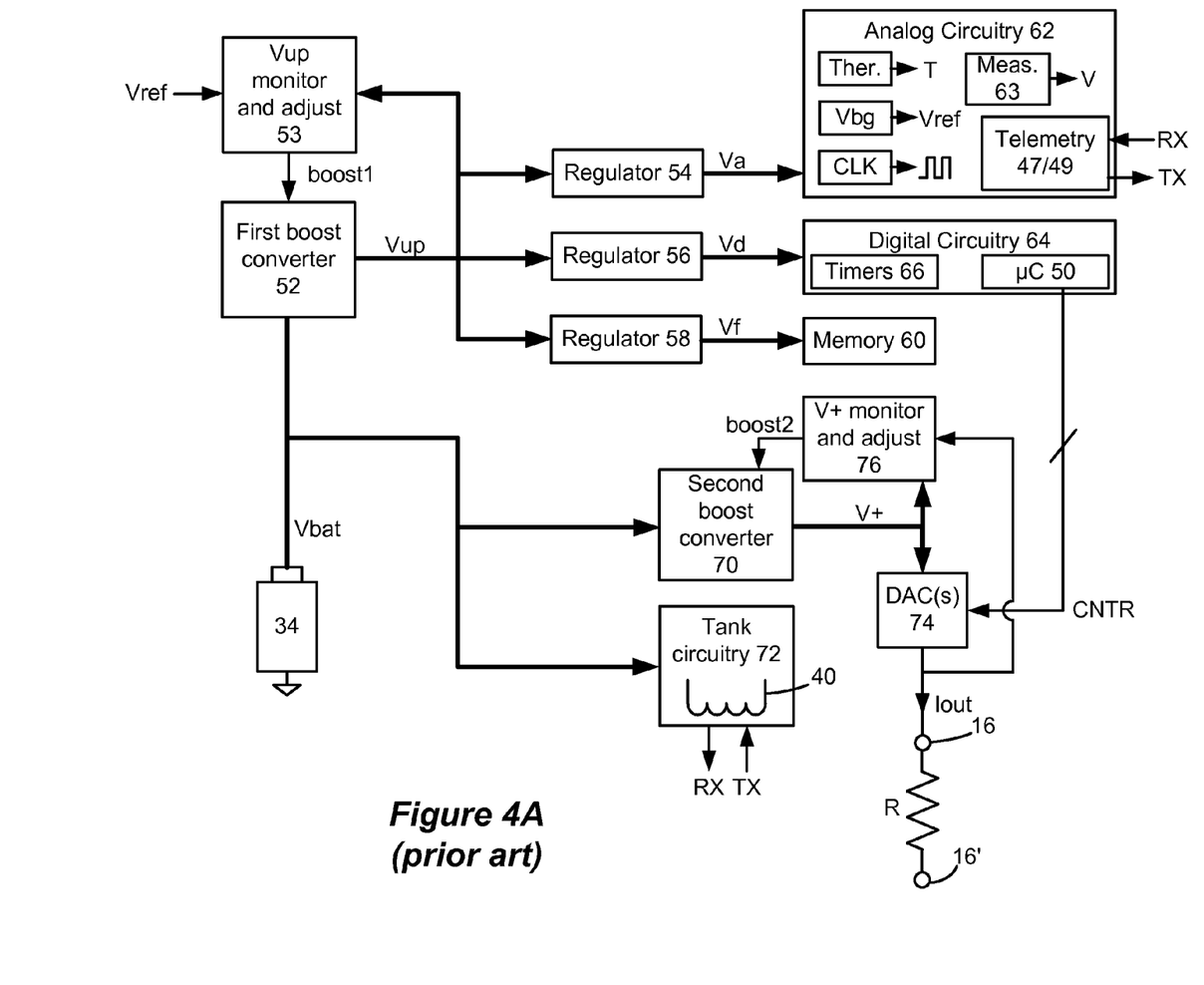
FIG. 4A shows the power supply architecture of the IPG.

FIG. 4A shows an architecture for IPG 10, which is described in U.S. Patent Application Publication 2013/0331910. Shown with particular emphasis are the various power supplies in the IPG 10, which are shown with thicker lines. Primary battery 34 provides the main power supply voltage, Vbat, from which all other power supply voltages in the IPG 10 are derived. Because Vbat is relatively small (e.g., around 3 Volts, but dropping as it depletes over the IPG 10's lifetime), and because certain circuits in the IPG 10 require higher power supply voltages than Vbat may be able to provide, the IPG 10 includes boost circuitry. In particular, IPG 10 includes a first boost converter 52 and a second boost converter 70, both of which comprise DC-DC converters for converting Vbat to different power supply voltages, i.e., to Vup and V+, as explained further below.

The first boost converter 52 generates power supply Vup, which comprises the power supply for most of the circuitry in the IPG 10, including analog circuitry 62, digital circuitry 64 (including microcontroller 50), and memory 60. Vup may be regulated (per regulators 54, 56, and 58) to derive separate power supply voltages Va, Vd, and Vf dedicated to each of these circuits. In one example, Vup can equal approximately 3.2 Volts, with low-drop-out regulators 54, 56, and 58 producing power supplies Va, Vd, and Vf of approximately 2.8 Volts. As the particulars of analog circuitry 62, digital circuit 64, and memory 64 are described in the above-cited '510 Application, they are not elaborated upon here. Vup is monitored via a monitor and adjust block 53, which compares Vup to a reference voltage, Vref, to determine whether Vup is too low. If so, this block 53 via control signal boost1 instructs the first boost converter 53 to operate, as explained further below.

The second boost converter 70 is used to generate a different power supply voltage, V+, called the compliance voltage, for powering the current generation circuitry 74 that produces the therapeutic current pulses (Iout) at one or more of the electrodes 16. In FIG. 4A, such current generation circuitry comprises one or more Digital-to-Analog converters (DAC(s) 74) that provide current pulses of the prescribed magnitude, frequency, and duration in accordance with digital control signals (CNTR). Because the prescribed current pulses can differ from time to time for a given patient, or from patient to patient, V+ is not fixed, but is instead set at an optimal level that is not too low to provide the prescribed current pulses, nor too high as to waste battery 34 power. Specifically, V+ monitor and adjust circuit 76 monitors a voltage drop across the DAC(s) 74, which it uses to control the second boost converter 70 to generate a power supply voltage V+ of an appropriate magnitude in accordance with control signal boost2. Again, further details regarding compliance voltage generation can be found in the above-cited '510 Application.

Figure 4B:
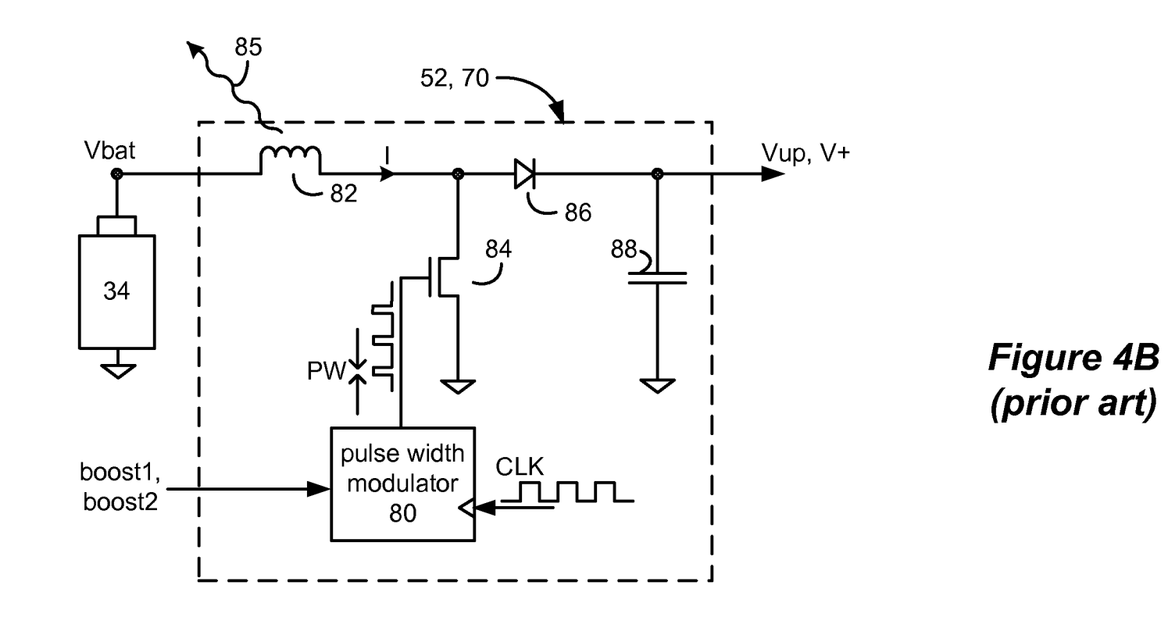
FIG. 4B shows boost converter circuitry used to generate higher power supply voltages, including an inductor that can interfere with a communication coil in the IPG.

Both the first boost converter 52 (producing Vup) and the second boost converter 70 (producing V+) can comprise the same basic circuitry as shown in FIG. 4B, which comprises a well-known inductor-based boost converter. When enabled via control signal boost1 or boost2, a pulse width modulator 80 modulates a pulse width (PW) of a clock signal (CLK), which is sent to the gate of a transistor 84. When the transistor 84 is on, current (I) passes through an inductor 82. When the transistor 84 is turned off, the current in the inductor 82 discharges through a diode 86 to a capacitor 88, whose top plate comprises Vup in the first boost converter 52, or the compliance voltage V+ in the second boost converter 70. Because the capacitor 88 was already charged to the battery voltage, Vbat, the additional charge from the inductor 82 boosts Vup or V+ to a value higher than Vbat, with diode 86 preventing this excess charge from dissipating backwards into the circuit. Capacitor 88, in addition to storing the charge, also filters and stabilizes Vup and V+. Thus, as the gate of transistor 84 oscillates between on and off, Vup or V+ continues to boost at a rate determined by the duty cycle of the gate pulse train. When control signal boost1 or boost 2 is disabled, oscillations at the gate of the transistor 84 are halted, which causes Vup or V+ to fall as charge is consumed by the circuitry to which these power supplies are connected. Of course, the particulars of the circuitry values used in the first and second boost converters 52 and 70 will differ in accordance with their different functions and the voltages they must produce. Control signals boost1 and boost2 may be digital or analog, and may comprise a digital or analog value indicating how "hard" the boost converter must work to produce the desired power supply voltage.

It is known that a boost converter has the potential to interfere with the telemetry circuitry operable in an IPG. See U.S. Patent Application Publication 2010/0211132, discussing this issue in the context of the second boost converter 70 that produces the compliance voltage, V+. This is because the boost converter, via the current I through its inductor 82, will produce a magnetic field 85 when it operates, which magnetic field 85 may couple to the communication coil 40 in the IPG. Even if the communication coil 40 has a high quality factor and good out-of-band noise rejection, the magnetic field 85 produced by inductor 82 may still have frequency components generally within the band of the communication coil (e.g., from 100 kHz to 150 kHz). Moreover, the frequency components present in magnetic field 85 can be difficult to control because they are dependent on the power supply voltage being produced by the boost converter at any given time. If interference by the inductor 82 is severe, telemetry may not be reliable. Interference by the inductor 82 during reception of data at the communication coil 40 is especially problematic, as the telemetry signal received by the communication coil 40 may be quite small in magnitude.

BRIEF DESCRIPTION OF THE DRAWINGS

FIGS. 5A and 5B show preferred and non-preferred orientations and placements of the boost converter's inductor within the IPG's communication coil, in accordance with an aspect of the invention, while

DETAILED DESCRIPTION

The design of IPG 10 is especially concerning with regarding to coupling between the communication coil 40 and the inductors 82 in either of the boost converters 52 or 70. Because of the size of the battery 34 within the case 30, the PCB 42 and communication coil 40 are relegated to a relatively small volume V in the case 30 between the battery 34 and the header 28, as shown in FIG. 2. Both the communication coil 40 and the PCB 42 are preferably made as large as possible within this volume V to increase the area of the communication coil 40 (which improves external communications) and to maximize the PCB 42's area for IPG electronics.

Figure 5A:
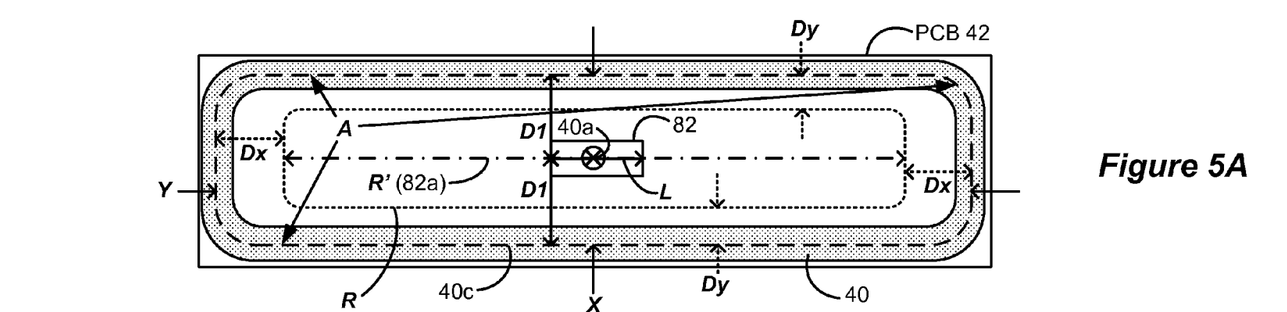
Figure 5B:
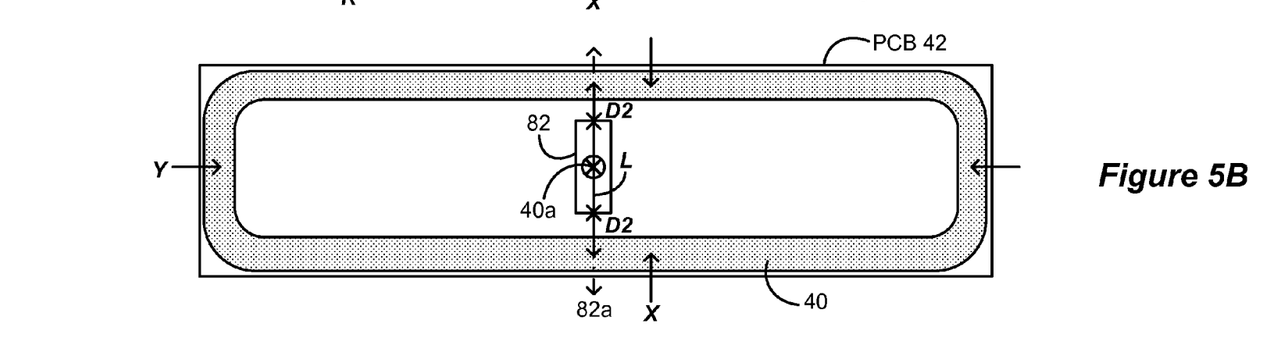
Figure 5C:
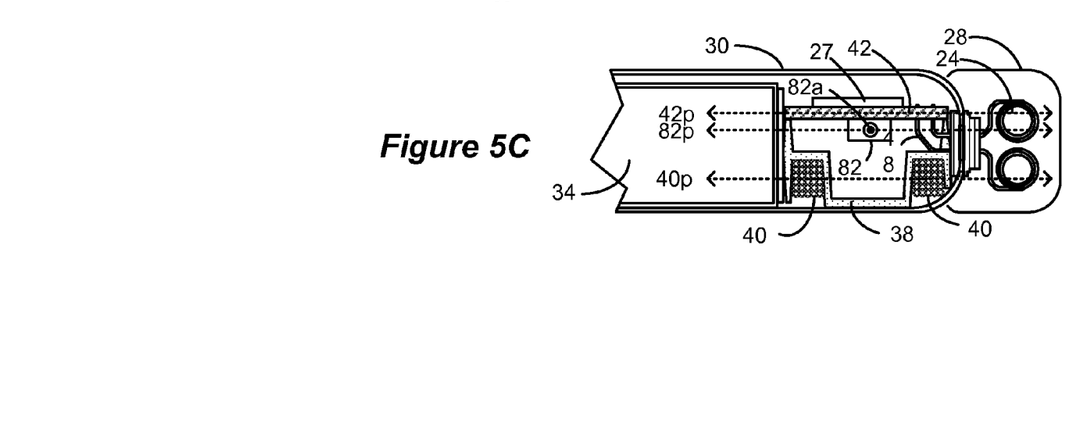
FIG. 5C shows the preferred orientation and placement in cross section.

As a result, and referring to FIG. 5A, the communication coil 40 proceeds around the periphery of the PCB 42, although in different parallel planes 40p and 42p as noted earlier. Because the inductors 82 of the boost converters 52 or 70 would be mounted to the PCB 42, they would also be within the area extent A of the communication coil 40 (FIG. 5A) as projected onto plane 82p in which the inductors 82 reside (FIG. 5C). Because inductors 82 are within the area extent A of the communication coil 40, they are closer and more prone to interfering with the communication coil 40 than they would be if placed outside of the communication coil 40. In particular, because the communication coil 40 of IPG 10 has minimum and maximum perpendicular dimensions X and Y, the inductors 82 must be at least somewhat close to the maximum dimensions Y. As shown, the communication coil 40's area extent A and dimensions X and Y are determined with respect to the coil's center circumference 40c, but could also be determined with respect to the coil's inner or outer circumferences as well.

Figure 6A:
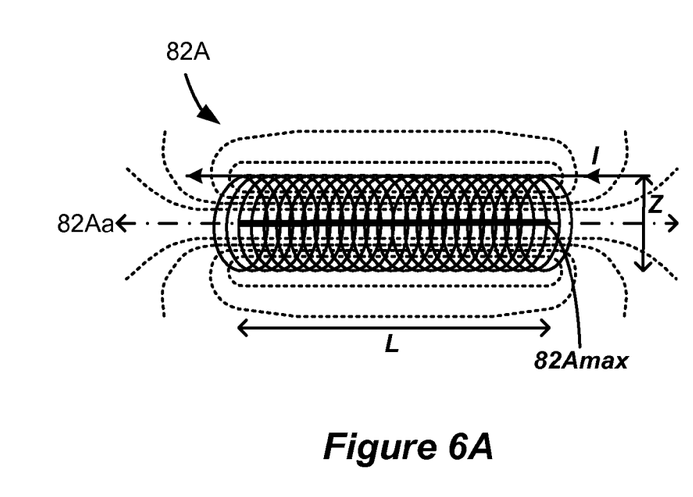
FIGS. 6A and 6B show various inductor designs useable for the boost converter, each having a length relevant to the orientations of FIGS. 5A and 5B.
Figure 6B:
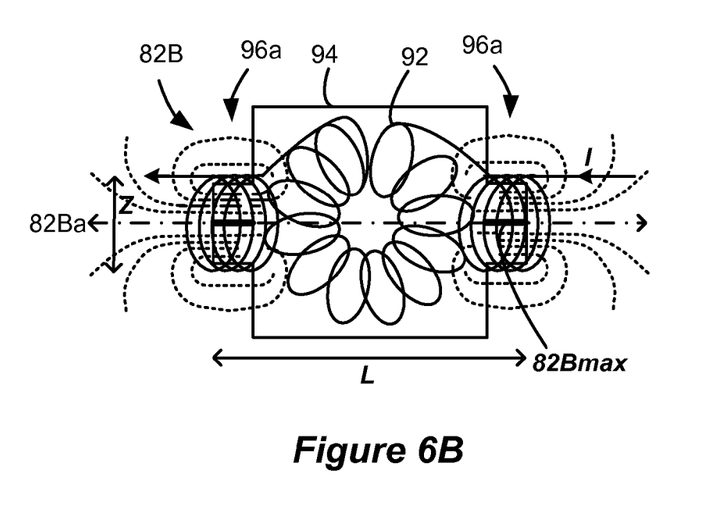
Figure 9A:
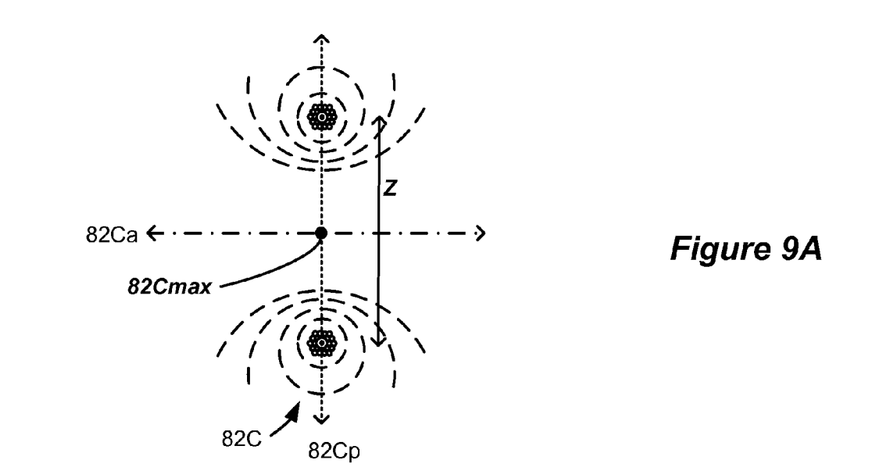
FIGS. 9A and 9B show application of the disclosed technique to inductors having no lengths along their axes.

The inventors have noticed that the orientation and placement of the boost converters' inductors 82 relative to the communication coil 40 affects the formers' interference with the latter in IPG 10, particularly where the inductor 82 has a length L. FIGS. 6A and 6B show shows different configurations for the inductors 82 useable in the boost converters 52 or 70. A helical inductor 82A is shown in FIG. 6A, which is wound around an axis 82Aa in the plane 82p of the inductor 82A (FIG. 5C). Inductor 82B in FIG. 6B comprises for example the 8300 Series of power inductors manufactured by Murata Manufacturing Co., Ltd., or the Micro-Pac Plus power inductor manufactured by Cooper Electronic Technologies. In this inductor design, the inductance is primarily governed by a toroid winding 92 within the inductor's 82B's package 94. However, the ends 96a and 96b are terminated by being wound around an axis 82Ba which is again in plane 82p. In either case, the winding around axes 82a define a length L for the inductor 82. (Dimension Z, which may comprise the diameter of the windings of inductors 82A and 82B, is also shown, although such dimension Z is ignored for the time being. Dimension Z is discussed later with respect to FIGS. 9A and 9B).

Also shown in dotted lines in FIGS. 6A and 6B are the magnetic flux lines produced by the inductors 82A and 82B as the boost converters operate. A largest magnetic field strength, 82max, can be identified, which as one skilled in the art will understand are at locations where the magnetic flux density is largest. For the inductor 82A of FIG. 6A, the largest magnetic field strength, 82Amax, occurs in a line along axis 82Aa inside of the inductor 82A. For the inductor 82B of FIG. 6B, the largest magnetic field strength, 82Bmax, again occurs along the axis 82Ba of the termination windings 96a and 96b, although occurring in two separate lines. (In reality, the largest magnetic field strength 82Bmax would also proceed in a circular shape through the toroid 92, but as the magnetic field is contained within and doesn't extend outside of the toroid, it can be ignored). The magnetic field strength is also relatively strong (although not maximal) extending from the ends of the lengths L of the inductors 82 along their axes 82a, where the magnetic flux density is still relatively high.

The inventors have determined that inductors 82 such as those shown in FIGS. 6A and 6B interfere with the communication coil 40 depending on their orientation, i.e., depending whether their lengths L, or their axes 82a, are parallel or perpendicular to the minimum X and maximum Y dimensions of the communication coil 40. The inventors in particular have determined that the inductor 82 in the first boost converter 52—that used to produce Vup—is especially problematic, although the inductor 82 in the second boost converter 70—that used to produce V+—is still of concern, as the above-cited '132 Publication discusses.

A preferred and lowest-interference orientation for the inductors 82 relative to the communication coil 40 is shown in FIG. 5A, in which the inductor's length L (axis 82a) is parallel with the maximum dimension Y, and perpendicular to the minimum dimension X. By contrast, the orientation of the inductor 82 in FIG. 5B, in which the inductor's length L (axis 82a) is perpendicular with the maximum dimension Y, and parallel to the minimum dimension X, induces more noise to the communication coil 40. For simplicity, only one inductor 82 of one of the boost converters 52 or 70 is shown, although the disclosed preferred orientations and placements are preferably applied to both inductors 82.

Figure 7A:
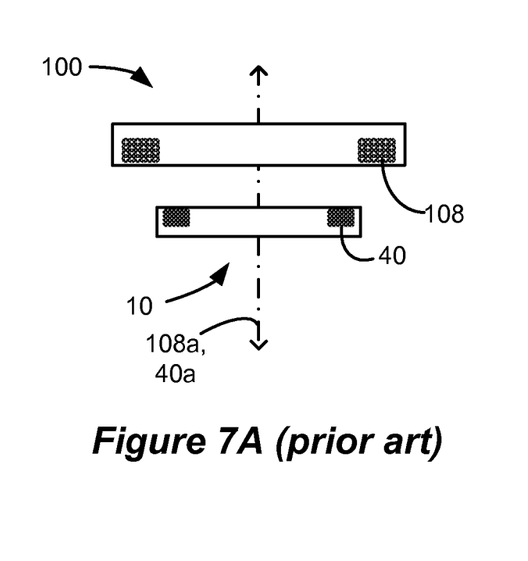
FIGS. 7A and 7B show inductive coupling between an IPG coil and an external controller coil, in accordance with the prior art.
Figure 7B:
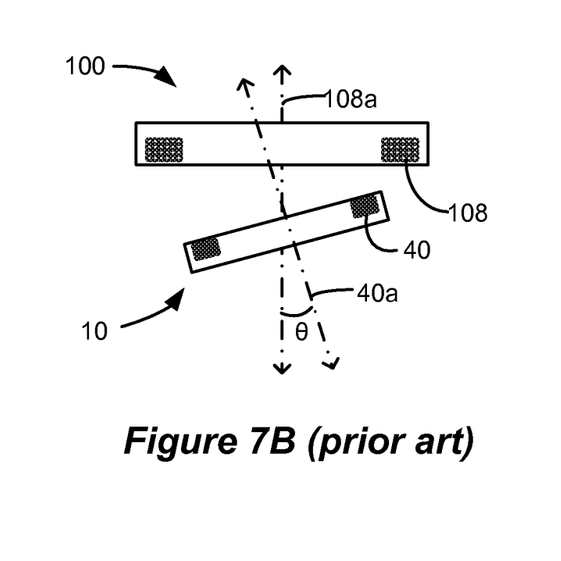

It is not evident that the orientations of the inductors 82 in the boost converters should differ significantly with respect to the noise imparted to the communication coil 40, because the inductors 82 are generally not well coupled to the communication coil 40 in a traditional sense understood for promoting data communications with the communication coil 40. As is known, good inductive coupling between the communication coil 40 in the IPG 10 and the coil 108 in the external controller 100 (FIG. 2) occurs if the axes 40a and 108a around which these coils are wound are parallel (and preferably collinear) as shown in FIG. 7A. See also U.S. patent application Ser. No. 61/887,237, filed Oct. 4, 2013. Coupling decreases as the angle θ between these axes 40a and 108a increases (FIG. 7B), and would be minimized when the axes 40a and 108a are orthogonal. Because the axes 82a of the inductors 82 and axis 40a of the communication coil 40 are orthogonal, one might not expect noise coupling from the inductors 82 to be significant, and hence might not expect that that orientation or placement of the inductors 82 relative to the communication coil 40 would matter.

Nonetheless, decreased coupling between the inductor 82 and the communication coil 40 in FIG. 5A results from minimizing overlap of the magnetic flux from inductor 82 and the communication coil 40, even if such coupling would seem to be insignificant for the reasons just described. When the inductor 82 is oriented as in FIG. 5A, a distance D1 between the ends of the length L of inductor 82 and the communication coil 40 is larger than the distance D2 in the orientation of FIG. 5B, which distances are measured with the inductor 82 placed equidistantly from the maximum dimensions Y of the communication coil 40. Moreover, the strength of the inductor 82's magnetic field is strongest along its axis 82a, making the decreased distance D2 of FIG. 5B that much more problematic. It should be noted that distances D1 and D2 may be not be planar as shown in FIGS. 5A and 5B if the inductor 82 and communication coil 40 are not in the same planes (as is the case for IPG 10). (It is also assumed that dimension Z of the inductor 82 (FIGS. 6A and 6B) is significantly less than the minimal dimension X of the communication coil 40, which may not always be the case in an actual implementation). Such distances D1 and D2 may also be determined with respect to other than the center circumference of the communication coil 40.

As well as showing an optimal orientation for the inductor 82, FIG. 5A additionally shows an optimal placement for the inductor 82 within the area extent A of communication coil 40, where the inductor 82 is placed at the communication coil's axis 40a. With this placement, the ends of the inductor 82's length L are equidistant from both the maximum Y and minimum X dimensions of the communication coil 40. The inventors consider this placement to be more important for the inductor in the first boost converter 52, which as discussed above is more prone to interfering with the communication coil 40.

Such optimal placement of the inductor 82 may not be possible depending on other circuitry present on the PCB 42, and is not strictly required. In other examples, the optimally-oriented inductor 82 can be placed within a region R within the area extent A of the communication coil 40, which region R may be limited by a threshold distance to the Y dimension (Dy) and a threshold distance to the X dimension (Dx). In a preferred embodiment, Dx is larger than Dy, which recognizes that relatively strong magnetic fields emanate from the ends of the length L of the inductor 82 along its axis 82a, and thus that a larger distance to the communication coil 40 is preferred along this axis 82a.

Region R (and distances Dx and Dy) may be determined with reference to the orientation and placement of the inductor 82 in FIGS. 5A and 5B. For example, R may be defined as the boundary at which coupling between the inductor 82 and the communication coil 40 increases by a set amount (e.g., 50%) when compared to the orientation and placement of FIG. 5A, or may defined as the boundary at which coupling decreases by a set amount (e.g., 50%) when compared to the orientation and placement of FIG. 5B. Other metrics or thresholds may also be used to set the boundary of preferred placement region R. Region R may also be constrained to one dimension. For example, in one example, Dy=D1, effectively restraining placement of the optimally-oriented inductor 82 along an axis R' parallel to and equidistant from the longer Y portions of the coil 40. Such placement is preferred for the inductors 82 in the boost converters 52 and 70 in IPG 10, with the inductor of the more-critical first boost converter 52 being placed on axis R' at or near the axis 40a of the coil 40, and with the inductor 82 of the less-critical second boost converter 70 also placed along axis R' but closer to the shorter portions X of the coil 40.

As alluded to earlier, the preferred orientation and placement of the boost converters' inductors 82 with respect to the communication coil 40 does not require the inductors 82 to be in the same plane 40p of the communication coil 40, i.e., that the axes 82a of the inductors 82 be in plane 40p of the communication coil 40. Instead, the axes 82a of the inductors 82 may be located in a different plane 82p parallel to plane 40p of the communication coil 40, as shown for IPG 10 in FIG. 5C. Although the inductors 82 and communication coil 40 are both proximate to the same side of the PCB 42 in IPG 10, this is not strictly necessary, and inductors 82 may be proximate to the other side of the PCB 42 as part of other circuitry 27 for example. The inductors 82 in the boost converters 52 and 70 may also appear on different sides of the PCB 42, with one placed as shown in FIG. 5C, and the other comprising part of circuitry 27. In other IPG examples, one or more of the inductors 82 and communication coil 40 may reside in the same plane. For example, one or more inductors 82 and communication coil 40 may both be affixed to a same side of the PCB 42, with the inductor(s) 82 inside of the coil 40's windings.

Figure 8A:
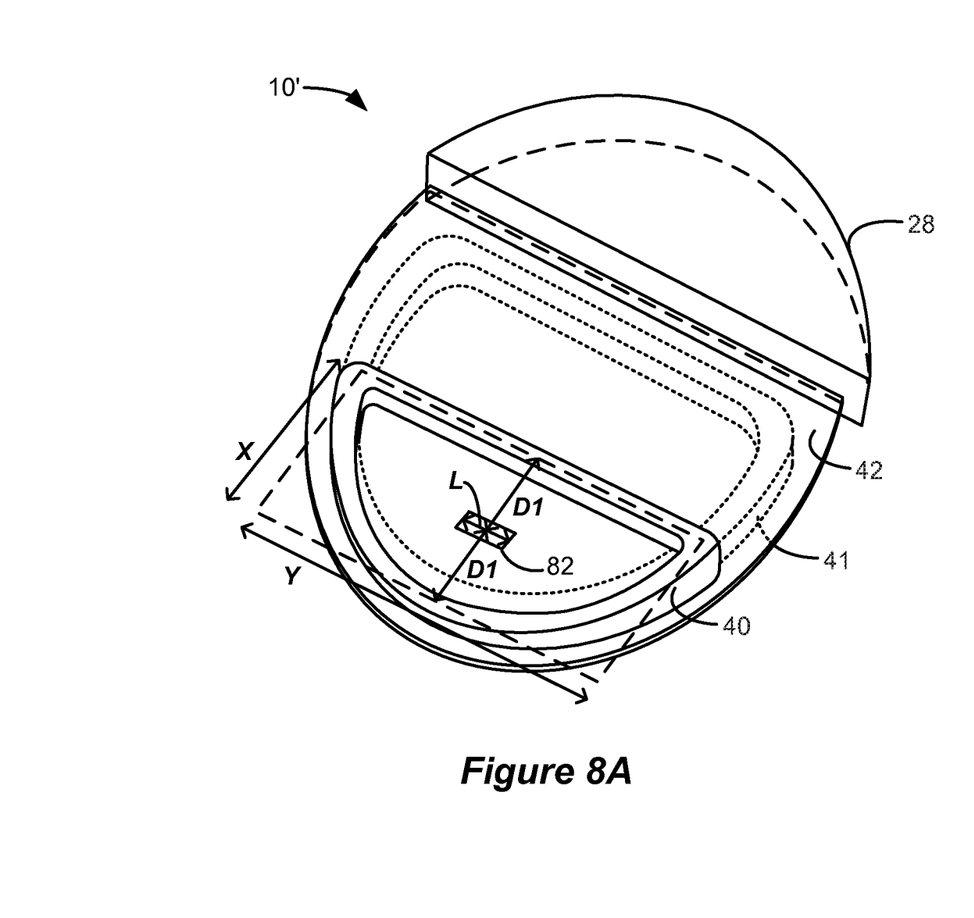
FIGS. 8A and 8B show application of the disclosed technique to communication coils of different shapes.
Figure 8B:
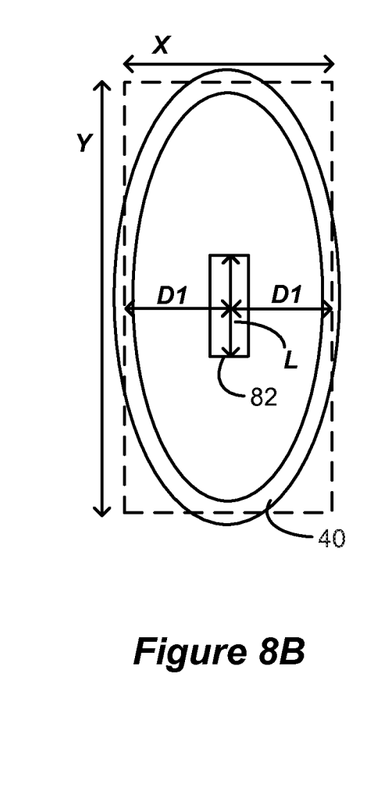

The preferred orientation and placement of the inductors 82 of the boost converters may be used with communication coils 40 that do not have readily recognizable maximum and minimum orthogonal dimensions X and Y. FIG. 8A for example shows an IPG 10' with a communication coil 40 generally shaped in a semi-circle, as disclosed in U.S. Patent Application Publication 2011/0112610. Although not rectangular in its shape, minimum and maximum orthogonal dimensions X and Y can still be identified by bounding the communication coil 40 (along any circumference) with a rectangle, as shown in dotted lines. A preferred orientation of an inductor 82 is achieved consistently with this disclosure's teachings by, in one example, orienting axis 82a of the inductor 82 parallel to the maximum dimension Y, and equidistantly to the communication coil 40 (D1). Such placement of inductor 82 preferably occurs at a maximum extent of the minimum dimension X, akin to the orientation and placement of FIG. 5A. FIG. 8B illustrates this same principle with respect to an oval-shaped communication coil 40, and again shows preferred orientation and placement of an inductor 82. Other modifications to the orientation and placement of the inductors 82 of FIGS. 8A and 8B may also be made, as described above.

Implementation of the disclosed technique can also be applied to inductors 82 of different shapes than those shown in FIGS. 6A and 6B. For example, in the cross section of FIG. 9A, an inductor 82C is shown comprising a flat coil (akin to communication coil 40) wound around an axis 82Ca and essentially wound in a single plane 82Cp. This inductor 82C has no length L along its axis 82Ca (ignoring the thickness of its windings), although it does have a dimension Z perpendicular to axis 82Ca between its windings (which dimension Z could comprise inductor 82C's diameter, as alluded to earlier).

Figure 9B:
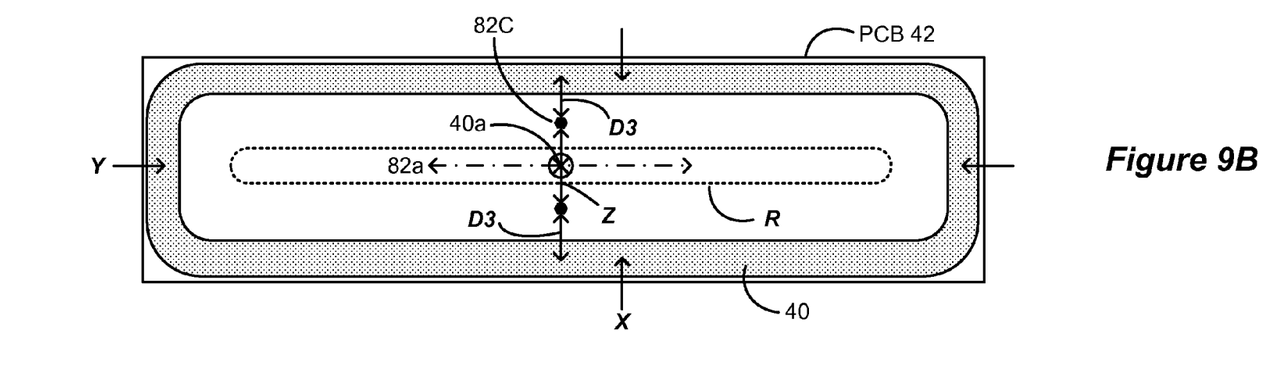

Despite this dimension Z, the preferred orientation for the inductor 82C can still be one in which the inductor's axis 82Ca is parallel to the maximum dimension Y, as shown in FIG. 9B. This results again from an understanding of the magnetic field strength of inductor 82C, as shown by the flux lines in FIG. 9A. The magnetic field strength of inductor 82C is strongest in the center of the inductor 82C (82Cmax), but is also relatively strong along its axis 82Ca, and may be stronger than the magnetic field around the windings at the same distance from the center of the inductor 82C. As such, it may be preferable to orient the inductor 82C as shown in FIG. 9B, even if this does not maximize the distance D3 between the inductor's windings and the communication coil 40. A region R around which the inductor 82C could be placed for this orientation while still providing suitably low coupling to the communication coil 40 can be determined consistent with earlier explanations.

Although focusing on reducing interference with the communication coil 40, it should be noted that the disclosed teachings regarding orientation and placement of the inductor 82 in the boost converters can assist in preventing interference by inductor 82 with other coils or inductors in the an IPG—for example, the charging coil 41 in FIG. 8A used to wirelessly receive power from an external charger. Likewise, the disclosed teachings can also be used to orient and place other inductors, coils, or components with wound terminations in the IPG (not associated with the boost converters) in manners to prevent interference with the communication coil 40.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device, comprising:
a coil comprising minimum and maximum orthogonal dimensions in a first plane and wound around a first axis; and
a boost converter configured to produce a second voltage from a first voltage, wherein the boost converter comprises an inductor wound around a second axis in a second plane comprising or parallel to the first plane, and wherein the second axis is parallel to the maximum dimension.

2. The device of claim 1, wherein the coil is configured to transmit and/or receive data to and/or from an external device by magnetic induction.

3. The device of claim 1, wherein the inductor has a length along the second axis.

4. The device of claim 1, further comprising a battery, wherein the first voltage comprises a voltage of the battery.

5. The device of claim 1, further comprising at least one regulator, wherein the at least one regulator is configured to produce from the second voltage at least one power supply voltage for circuitry in the implantable medical device.

6. The device of claim 1, further comprising current generation circuitry configured to produce a therapeutic current at at least one electrode, wherein the second voltage comprises a power supply voltage for the current generation circuitry.

7. The device of claim 6, wherein the boost converter receives a voltage drop across the current generation circuitry, and wherein the boost converter is configured to produce the power supply voltage for the current generation circuitry in accordance with the voltage drop.

8. The device of claim 1, further comprising a circuit board, wherein the coil and the inductor are on a same side of the circuit board.

9. The device of claim 1, wherein the coil is rectangular.

10. The device of claim 1, wherein the inductor is within an area extent of the coil.

11. The device of claim 10, wherein the inductor has a length along the second axis, and wherein the second axis is equidistant from the maximum dimensions of the coil.

12. The device of claim 10, wherein the inductor has no length along the second axis, and wherein the inductor comprises a dimension perpendicular to the second axis, wherein the dimension is equidistant from the maximum dimensions of the coil.

13. The device of claim 1, wherein inductor is placed at the first axis and is equidistant from the maximum dimensions of the coil.

14. The device of claim 1, wherein the minimum and maximum orthogonal dimensions are determined by bounding the coil with a rectangle.

15. An implantable medical device, comprising:
a communication coil configured to transmit and/or receive data to and/or from an external device by magnetic induction, the communication coil comprising minimum and maximum orthogonal dimensions in a first plane and wound around a first axis; and
an inductor wound around a second axis in a second plane comprising or parallel to the first plane, wherein the inductor is within an area extent of the communication coil, and wherein the second axis is parallel to the maximum dimension.

16. The device of claim 15, further comprising a boost converter configured to produce a second voltage from a first voltage, wherein the inductor comprises a component of the boost converter.

17. The device of claim 16, further comprising a battery, wherein the first voltage comprises a voltage of the battery.

18. The device of claim 17, further comprising at least one regulator, wherein the at least one regulator is configured to produce from the second voltage at least one power supply voltage for circuitry in the implantable medical device.

19. The device of claim 16, further comprising current generation circuitry configured to produce a therapeutic current at at least one electrode, wherein the second voltage comprises a power supply voltage for the current generation circuitry.

20. The device of claim 15, further comprising a circuit board, wherein the communication coil and the inductor are on a same side of the circuit board.

21. The device of claim 15, wherein the inductor has a length along the second axis, and wherein the second axis is equidistant from the maximum dimensions of the communication coil.

22. The device of claim 15, wherein the inductor has no length along the second axis, and wherein the inductor comprises a dimension perpendicular to the second axis, wherein the dimension is equidistant from the maximum dimensions of the communication coil.

23. The device of claim 15, wherein inductor is placed at the first axis and is equidistant from the maximum dimensions of the communication coil.

24. The device of claim 15, wherein the inductor comprises a toroid with termination windings wound around the second axis, wherein the termination windings define a length of the inductor along the second axis.

* * * * *